United States Patent [19]

Massardo et al.

[11] Patent Number: 5,089,525
[45] Date of Patent: Feb. 18, 1992

[54] N-(HALOBENZOYL)-N'-2-HALO-4-(1,1,2-TRI-FLUORO-2-(TRIFLUORO-METHOXY)E-THOXY)-PHENYL-UREAS WITH INSECTICIDAL ACTIVITY

[75] Inventors: Pietro Massardo, Milan; Giovanni Meazza, Saronno; Franco Bettarini, Novara; Paolo Castoro, Vercelli; Vincenzo Caprioli, Pavia, all of Italy

[73] Assignee: Istituto Guido Donegani S.p.A., Milan, Italy

[21] Appl. No.: 239,996

[22] Filed: Sep. 2, 1988

[30] Foreign Application Priority Data

Sep. 4, 1987 [IT] Italy ............... 21794 A/87

[51] Int. Cl.⁵ ............... C07C 273/00; A01N 47/28
[52] U.S. Cl. ............... 514/594; 564/44
[58] Field of Search ............... 504/44; 514/594

[56] References Cited

U.S. PATENT DOCUMENTS 4,564,639  1/1986  Nagase et al. ............... 564/44

FOREIGN PATENT DOCUMENTS 203618  12/1986  European Pat. Off. .
0271923  6/1988  European Pat. Off. ............... 564/44
0277748  8/1988  European Pat. Off. ............... 564/44
0293943  12/1988  European Pat. Off. ............... 564/44
3613062  10/1987  Fed. Rep. of Germany ............... 564/44
212463  12/1984  Japan ............... 564/44
2182329  5/1987  United Kingdom ............... 564/44

Primary Examiner—C. Warren Ivy
Assistant Examiner—Raymond Covington
Attorney, Agent, or Firm—Morgan & Finnegan

[57] ABSTRACT

A class of particularly active insecticidal compounds: N-(halobenzoyl)-N'-2-halo-4-[1,1,2-trifluoro-2-(trifluoromethoxy)ethoxy]-phenyl-ureas, the preparation of such compounds and their use against infestations by insects.

8 Claims, No Drawings

N-(HALOBENZOYL)-N'-2-HALO-4-(1,1,2-TRI-FLUORO-2-(TRIFLUORO-METHOXY)ETHOXY)-PHENYL-UREAS WITH INSECTICIDAL ACTIVITY

DESCRIPTION OF THE INVENTION

1. Field of the Invention

The present invention relates to a class of insecticidal compounds, and more precisely it relates to N-(halobenzoyl)-N'-2-halo-4-[1,1,2-trifluoro-2-(trifluoromethoxy)ethoxy]-phenyl-ureas, endowed with a high insecticidal activity, and suitable for use in the agrarian, forestry, civil and veterinary fields in the fight against infestations by insects. These compounds are particularly active against eggs and larvae of insects.

2. Background of the Invention

In European Patent Application No. 203,618, insecticidal compounds are disclosed which are derivatives of 1-benzoyl-3-aryl-ureas having the formula:

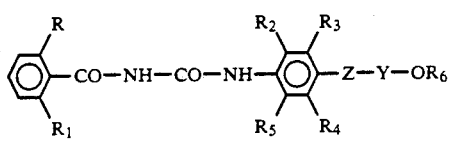

wherein
R = Cl, F;
$R_1$ = H, Cl, F.,
$R_2$ and $R_5$, which can be either equal to or different from each other, are: H, halogen, ($C_1$-$C_4$)-alkyl;
$R_3$ and $R_4$, which can be either equal to or different from each other, are: H, halogen, alkyl, haloalkyl, halo-alkenyl-oxy or alkynyl;
Z = O, S, or an $NR_7$ group, wherein $R_7$ is either ($C_1$-$C_3$)-alkyl or H;
Y = ($C_1$-$C_4$)-alkylene, halo-ethylene or halo-ethenyl
$R_6$ = ($C_1$-$C_4$)-alkyl; ($C_1$-$C_4$)-halo-alkyl; ($C_3$-$C_4$)-alkenyl;
($C_3$-$C_4$)-halo-alkenyl; ($C_3$-$C_4$)-cycloalkyl; ($C_3$-$C_4$)-halo-cycloalkyl; or ($C_3$-$C_4$) halo-cycloalkenyl.

During studies on the compounds disclosed in the above-mentioned European patent application, it has been discovered (in accordance with the present invention) that, among the compounds having formula (I), a particular class or subclass of compounds, i.e., N-(halobenzoyl)-N'-2-halo-4-[1,1,2-trifluoro-2-(trifluoromethoxy)ethoxy]-phenyl-ureas, exists which is surprisingly endowed with a decidedly higher insecticidal activity than that of analogous compounds.

DETAILED DESCRIPTION OF THE INVENTION

The object of the present invention is therefore the class of compounds N-(halobenzoyl)-N'-2-halo-4-[1,1,2-trifluoro-2-(trifluoro-methoxy)ethoxy]-phenyl-ureas having the formula:

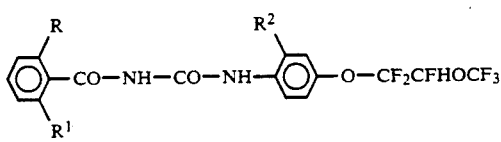

wherein:
R, $R^1$, which may be either equal to or different from each other, are H, F or Cl; at least one of R and $R^1$ being F or Cl, and
$R^2$ is either F or Cl.

The compounds of formula (II) are endowed with a particularly high insecticidal activity unexpectedly higher than the insecticidal activity displayed by the analogous compounds of formula (I) which have been disclosed in the above-mentioned European patent application.

Compounds having formula (II) may be used as such, or in the form of suitable compositions, in the fight against infestations by noxious insects.

Further objects of the present invention are hence the use of the compounds of formula (II) in the fight against insects, and the insecticidal compositions which contain a compound of the formula (II) as the active principle.

The preparation of the compounds of formula (II) is carried out by means of the reaction, as already generally described in the above mentioned European patent application, between a benzoyl isocyanate and an aromatic amine; and in particular by means of the reaction between a halo-benzoyl-isocyanate (III) and a 2-halo-4-[1,1,2-trifluoro-2-(trifluoromethoxy)ethoxy]-aniline (IV), according to the following equation:

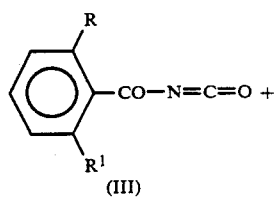

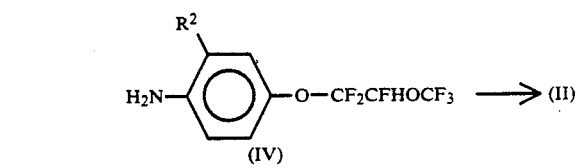

wherein R, $R^1$ and $R^2$ have the same meanings as stated above for formula (II).

The reaction does not require the presence of catalysts, and is carried out in an inert solvent and at a temperature between 0° C. and the boiling temperature of the mixture.

Benzoylisocyanates having formula (III) are known compounds, and may be prepared by per se known methods. The amines of formula (IV) may be prepared according to known methods; and, more precisely, they may be prepared according to the methods as disclosed in the above-mentioned European patent application, preferably by reacting the sodium or potassium salt of a 3-halo-4-aminophenol (V) of formula:

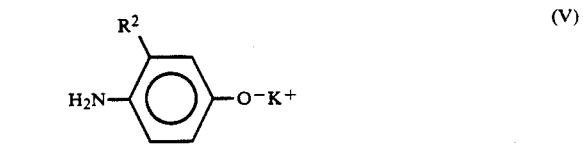

wherein $R^2$ has the same meaning as stated above for formula (II), with perfluorovinyl-perfluoromethyl-ether (VI) having the formula:

$$CF_2=CF-OCF_3 \quad (VI)$$

in polar aprotic solvents, at temperatures within the range of from 0° C. to room temperature.

The ethers of formula (VI) may be prepared according to methods known from the prior art, as described, e.g., in J. Org. Chem., 48, 242 (1983).

An alternative route for the synthesis of the compounds of formula (II) consists in reacting a halobenzamide (VII) with a 2-halo-4-[1,1,2-trifluoro-2-(trifluoromethoxy)-ethoxy]-phenyl-isocyanate (VIII) according to the equation:

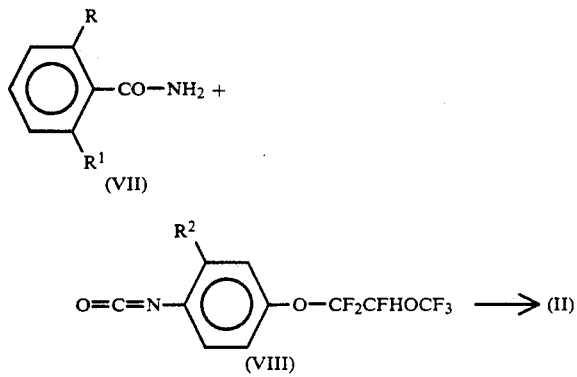

wherein R, $R^1$ and R2 have the same meanings as stated above for formula (II).

Such reaction is carried out under conditions analogous to such conditions as are disclosed for the reaction between benzoyl-isocyanates of formula (III) and the amines of formula (IV).

As has been previously mentioned, the compounds of formula (II) are endowed with a high insecticidal activity, with a particularly high activity being above all displayed against insect eggs and larvae. Among these, in particular, the compounds having formula (II) are especially effective in combatting insects belonging to the Lepidoptera, Diptera, and Coleoptera orders.

These orders comprise a large number of species notable for their noxiousness in the agrarian, forestry, civil and veterinary fields. Thus, the compounds of formula (II) are especially effective for many uses, such as, e.g., the defense of agrarian culrivations against infestations by phytophagous insects, the protection of sites infested by mosquitos and flies, the protection of breeding-cattle against certain cattle parasites, and so forth.

For practical uses, the compounds of formula (II) may be used as such or, more satisfactorily, in the form of compositions containing, besides one or more of the compounds of the above formula (II) as the active ingredient or principle, also solid or liquid inert carriers and, optionally, still further additives. According to the usual formulation practice, the compositions may be supplied as wettable powders, emulsifiable concentrates, etc.

The amount of active principle constituted by one or more compounds of formula (II) in the compositions may vary over a wide range, such as 1 to 95% by weight, depending on the type of composition and on the use for which it is intended.

Furthermore, the amount of active substance to be distributed for the insecticidal treatments will depend on various factors, such as, e.g., the type of infestation, the environment wherein the infestation is occurring (agrarian cultivations, ponds or watercourses, organic substrates of various kinds), the type of composition used, climatic and environment factors, available application means, and so forth. In general, amounts of the active substance within the range of from 0.01 to 1 kg/ha are sufficient for a good disinfestation.

EXAMPLES

The following examples are given for the purpose of better illustrating the invention, but without limiting it in any way:

EXAMPLE 1

Preparation of N-(2,6-difluorobenzoyl)-N'-2-fluoro-4--[1,1,2-trifluoro-2-(trifluoromethoxy)ethoxy]-phe (Compound No. 1)

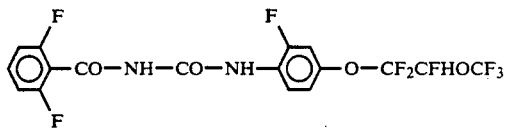

To a four-necked flask of 500 ml capacity, fitted with a condenser, thermometer, dropping funnel, and mechanical stirring means, 23 g of 2-fluoro-4-[1,1,2-trifluoro-2-(trifluoromethoxy)ethoxy]-aniline dissolved in 200 ml of anhydrous ethyl ether are charged under nitrogen.

14.3 g of 2,6-difluoro-benzoyl-isocyanate dissolved in 50 ml of anhydrous ethyl ether are then added dropwise at room temperature.

The reaction mixture is refluxed with stirring for 1 hour; it is then cooled to 0° C., filtered under nitrogen, the precipitate is washed with cold n-hexane and finally dried under nitrogen.

32.4 g (87%) of the title compound having a melting point of 139° C. are finally obtained.

EXAMPLE 2

By starting from the anilines disclosed in Example 3 below, and by operating under conditions analogous to those as disclosed above in Example 1, by using 2,6-difluoro-benzoyl-isocyanate, the following compound is obtained:

Compound No. 2: N-(2,6-difluorobenzoyl)-N'-2-chloro-4-[1,1,2-trifluoro-2-(trifluoromethoxy)-ethoxy]-phenyl-urea:

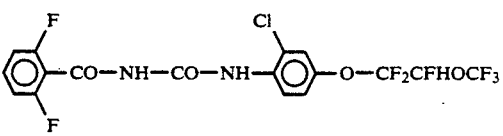

melting point [m.p.]=147° C.

Whilst by using 2-chlorobenzoyl-isocyanate, the following compounds were prepared:

Compound No. 3: N-2-chlorobenzoyl-N'-2-fluoro-4-[1,1,2-trifluoro-2-(trifluoromethoxy)-ethoxyl]-phenyl-urea:

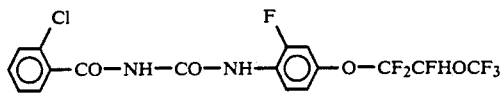

m.p. = 127° C.

Compound No. 4: N-2-chlorobenzoyl-N'-2-chloro-4-[1,1,2-trifluoro-2-(trifluoromethoxy)-ethoxy]-phenyl-urea:

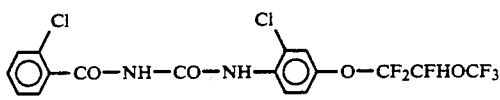

m.p. = 116° C.

EXAMPLE 3

Preparation of the Intermediate Anilines

To a three-necked flask of 100 ml capacity fitted with thermometer, pierceable cap for withdrawing the contents, connection to a supply of perfluorovinyl-perfluoromethyl-ether gas, and magnetic stirrer, 1.27 g of 3-fluoro-4-amino-phenol dissolved in 40 ml of a mixture constituted by toluene and dimethyl-sulphoxide in the ratio of 8:2 by volume are charged under nitrogen. 100 mg of finely ground KOH at 85% are added, the system is evacuated and from the gas supply 1.66 g of perfluorovinyl-perfluoromethyl-ether are added.

The reaction is allowed to proceed at room temperature for one hour, the reaction mixture is then poured into 100 ml of water, and is extracted with ethyl ether. The ethereal phase is thoroughly dried over sodium sulphate and is concentrated; 2.8 g of 2-chloro-4-[1,1,2-trifluoro-2-(trifluoromethoxy)-ethoxy]-aniline are obtained.

The proton nuclear magnetic resonance spectrum ($^1$H-N.M.R.) has the following characteristics: $^1$H-N.M.R.(CDCl$_3$): 6.9–6.4 (m, 3H, aromatic); 6.25–5.35 (dt, IH, —CFH—); 3.55 (s, 2H, -NH$_2$).

By operating under the above conditions, but using 3-chloro-4-amino-phenol and CF$_2$=CF—O—CF$_3$, 2-chloro-4-[1,1,2-trifluoro-2-(trifluoromethoxy)-ethoxy]-aniline was obtained:

$^1$H-N.M.R.(CDCl$_3$) 7.3–6.7 (m, 3H, aromatic); 6.6–5.7 (dt, 1H, —CFH); 3.7 (bs, 2H, —NH$_2$).

The abbreviations in the spectra have the following meanings:
s = singlet;
m = multiplet, or unresolved complex signal;
t = triplet
d = doublet;
b (broad) = broad signal;

EXAMPLE 4

Determination of the Insecticidal Activity

Test 1

Immediate Residual Activity on larvae of *Spodoptera littoralis* (Lepidoptera)

Tobacco leaves are treated by mechanical spraying with a water-acetonic solution of the product under test at 10% by volume of acetone, and containing a conventional surfactant.

After the complete evaporation of the solvents, the leaves are infested with second-age larvae of the lepidopreran.

The infested leaves are stored in a suitably conditioned room throughout the test.

Infested and stored in a similar way are tobacco leaves treated with the water-acetonic solution (at 10%) only, and with the same surfactant, for use for comparison purposes as the control group.

Ten days after the infestation, and after renewing the treated substrate at least once, the dead larvae are counted, and compared to those of the control group.

Test 2

Activity on Larvae of Aedes aegypti (Diptera)

Spring water (297 ml) is mixed with an acetonic solution (3 ml) of the product under test, at a suitable concentration.

Into the resulting solution are introduced 25 4-day-old larvae of the mentioned dipreran, which are suitably fed during the whole observation time period. As the control group, other larvae are introduced into a water-acetonic solution (297 ml of spring water, 3 ml of acetone) but without any active substances.

The number of dead larvae and pupae, or of adult insects normally emerged from the cocoon is noted every 2-3 days, until the end of the insects emergence from the cocoons of the control group.

The activity of the product being tested is expressed as the percentage of dead individuals relative to the total number of treated individuals, possibly corrected (in case of partial death in the control group) according to W. S. Abbott, "A Method of Computing the Effectiveness of an Insecticide", J. Econ. Enthomol., No. 18, pages 265–7 (1925).

In the following Table 1, the data relating to the insecticidal activity at the indicated doses, expressed as parts per million of active substance, are reported.

For both tests, 4 repeated tests for each dosage were taken into consideration, and a number of tests were carried out at different times, which is regarded as sufficient in order to give statistical significance to small differences in efficacy (with the dosage remaining the same).

TABLE 1

| Compound No. | | Insecticidal Activity | | | | | | | | | | | | |
|---|---|---|---|---|---|---|---|---|---|---|---|---|---|---|
| | | 1 | | 2 | | 3 | | 4 | | Ref. 1 | | Ref. 2 | | Ref. 3 | |
| | | Dosage ppm | Death rate % | Dosage ppm | Death rate % | Dosage ppm | Death rate % | Dosage ppm | Death rate % | Dosage ppm | Death rate % | Dosage ppm | Death rate % | Dosage ppm | Death rate % |
| Test No. 1 | | 0.005 | 100 | 0.01 | 100 | 0.01 | 100 | 0.01 | 100 | 1.0 | 100 | 1.0 | 100 | 0.1 | 100 |
| | | 0.001 | 97 | 0.005 | 95 | 0.005 | 98 | 0.005 | 85 | 0.5 | 70 | 0.5 | 95 | 0.05 | 93 |
| | | 0.0005 | 64 | 0.001 | 75 | 0.001 | 75 | 0.001 | 77 | 0.1 | 35 | 0.1 | 78 | 0.01 | 78 |
| | | | | | | | | | | | | 0.05 | 40 | 0.005 | 31 |
| Test No. 2 | | 0.0002 | 100 | n.d. | | 0.0002 | 100 | n.d. | | 0.2 | 100 | 0.02 | 100 | n.d. | |
| | | 0.00002 | 88 | | | 0.00002 | 90 | | | 0.02 | 25 | 0.002 | 86 | | |
| | | 0.000002 | 80 | | | 0.000002 | 77 | | | | | 0.0002 | 41 | | |

TABLE 1-continued

| | Insecticidal Activity | | | | | | | | | | | | | |
|---|---|---|---|---|---|---|---|---|---|---|---|---|---|---|
| | 1 | | 2 | | 3 | | 4 | | Ref. 1 | | Ref. 2 | | Ref. 3 | |
| Compound No. | Dosage ppm | Death rate % | Dosage ppm | Death rate % | Dosage ppm | Death rate % | Dosage ppm | Death rate % | Dosage ppm | Death rate % | Dosage ppm | Death rate % | Dosage ppm | Death rate % |
| | | | | | 0.0000002 | 71 | | | | | | | | |

As the reference 1, the compound: N-2,6-difluorobenzoyl-N'-4-[1,1,2-trifluoro-2-(trifluoromethoxy)ethoxy]-phenyl-urea.
As the reference 2, the compound: N-2,6-difluorobenzoyl-N'-4-[1,1,2-trifluoro-2-(perfluoroethoxy)ethoxy]-phenyl-urea.
As the reference 3, the compound: N-2-(chlorobenzoyl)-N'-3,5-dicloro-4-(1,1,2-trifluoro-2-(trifluoromethoxy)ethoxy-phenyl urea.
Said compounds are comprised in European patent application No. 203,618.

Although the invention has been described in conjunction with specific embodiments, it is evident that many alternatives and variation will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. N-(halobenzoyl)-N'-2-halo-4-[1,1,2-triflouro-2-(trifluoromethoxy)ethoxyl]-phenyl-ureas having the formula:

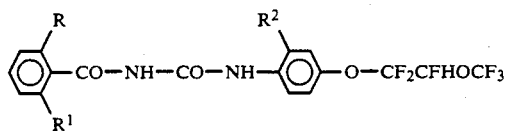

wherein:
R, R$^1$, which can be either equal to or different from each other, are H, F or Cl; at least one of R and R$^1$ being either F or Cl; and
R$^2$ is either F or Cl.

2. A compound according to claim 1 which is N-(2,6-difluorobenzoyl)-N'-2-fluoro-4[1,1,2-trifluoro-2-(trifluoromethoxy)-ethoxy]-phenyl-urea.

3. A compound according to claim 1 which is N-(2,6-difluorobenzoyl)-N'-2-chloro-4-[1,1,2-trifluoro-2-(trifluoromethoxy)-ethoxy]-phenyl-urea.

4. A compound according to claim 1 which is N-2-chlorobenzoyl-N'-2-fluoro-4-[1,1,2-trifluoro-2-(trifluoromethoxy)-ethoxy]-phenyl-urea.

5. A compound according to claim 1 which is N-2-chlorobenzoyl-N'-2-chloro-4-[1,1,2-trifluoro-2-(trifluoromethoxy)-ethoxy]-phenyl-urea.

6. Method for fighting infestations caused by noxious insects, consisting essentially in distribution on the infested area an effective amount of at least one compounds of claim 1.

7. Insecticidal compositions containing as the active ingredient a pesticidally effective amount of at least one of the compounds of claim 1, together with solid or liquid in carrier.

8. Insecticidal compositions containing as the active ingredient a pesticidally effective amount of at least one of the compounds of claim 7, wherein the insecticidal compositions includes other additives.

* * * * *